US00RE39175E

(19) United States
(12) Reissued Patent
Gaddy et al.

(10) Patent Number: US RE39,175 E
(45) Date of Reissued Patent: Jul. 11, 2006

(54) MICROBIAL PROCESS FOR THE PREPARATION OF ACETIC ACID AS WELL AS SOLVENT FOR ITS EXTRACTION FROM THE FERMENTATION BROTH

(75) Inventors: James L. Gaddy, Fayetteville, AR (US); Edgar C. Clausen, Fayetteville, AR (US); Ching-Whan Ko, Fayetteville, AR (US); Leslie E. Wade, Pearland, TX (US); Carl V. Wikstrom, Benton, AR (US)

(73) Assignees: Bioengineering Resources, Inc., Fayetteville, AR (US); Celanese International Corporation, Dallas, TX (US)

(21) Appl. No.: 11/149,502

(22) PCT Filed: Sep. 7, 1999

(86) PCT No.: PCT/US99/20416

§ 371 (c)(1),
(2), (4) Date: Mar. 7, 2001

(87) PCT Pub. No.: WO00/14052

PCT Pub. Date: Mar. 16, 2000

Related U.S. Patent Documents

Reissue of:
(64) Patent No.: 6,368,819
Issued: Apr. 9, 2002
Appl. No.: 09/786,544
Filed: Mar. 7, 2001

U.S. Applications:
(60) Provisional application No. 60/099,438, filed on Sep. 8, 1998, provisional application No. 60/099,439, filed on Sep. 8, 1998, provisional application No. 60/099,440, filed on Sep. 8, 1998, and provisional application No. 60/099,475, filed on Sep. 8, 1998.

(51) Int. Cl.
*C12P 39/00* (2006.01)
*C12P 7/54* (2006.01)

(52) U.S. Cl. ..... 435/42; 435/140; 435/170; 435/252.7

(58) Field of Classification Search ..... 435/42, 435/140, 170
See application file for complete search history.

(56) References Cited

U.S. PATENT DOCUMENTS 4,720,577 A * 1/1988 Wojtech et al.
5,173,429 A * 12/1992 Gaddy et al.
5,254,465 A * 10/1993 Wise
5,254,665 A * 10/1993 Crews et al.
5,593,886 A * 1/1997 Gaddy
5,807,722 A 9/1998 Gaddy
6,136,577 A 10/2000 Gaddy
6,753,170 B1 6/2004 Gaddy
2004/0236149 A1 11/2004 Gaddy

FOREIGN PATENT DOCUMENTS

WO WO-98/00558 A1 1/1998

OTHER PUBLICATIONS

Ricker et al., "Solvent Extraction with amines for recovery of acetic acid from dilute aqueous industrial streams"J. Sep Proc. Tech. 1980 1 (2) pp. 23–30 1980.*
Gaddy, J. "Biological Production of Products from Waste Gases", U.S. Appl. No. 09/219,395, filed Dec. 23, 1998.*
Ricker et al., "Solvent properties of organic bases for extraction of acetic acid from water", *J. Sep. Proc. Technol.* 1979 1(1):36–41.
J. Vega et al., "The Biological Production of Ethanol from Synthesis Gas", Applied Biochemistry and Biotechnology, 20/21 781–797 (1989).*
J. Vega et al., "Study of Gaseous Substrate Fermentations: Carbon Monoxide Conversion to Acetate. 2. Continuous Culture", Biotechnology and Bioengineering, 34:785–793 (1989).*
K. Klasson et al., "Bioconversion of Synthesis Gas into Liquid or Gaseous Fuels", Enzyme Microb. Technol., 14:602–608 (Aug., 1992).*
K. Klasson et al., "Biological Production of Liquid and Gaseous Fuels from Synthesis Gas", Applied Biochemistry and Biotechnology, 24/25:857–873 (1990).*

* cited by examiner

*Primary Examiner*—Herbert J. Lilling
(74) *Attorney, Agent, or Firm*—Howson and Howson

(57) ABSTRACT

A modified water-immiscible solvent useful in the extraction of acetic acid from aqueous streams is a substantially pure mixture of isomers of highly branched di-alkyl amines. This solvent is substantially devoid of mono-alkyl amines and alcohols. Solvent mixtures formed of such a modified solvent with a desired cosolvent, preferably a low boiling hydrocarbon which forms an azeotrope with water are useful in the extraction of acetic acid from aqueous gaseous streams. An anaerobic microbial fermentation process for the production of acetic acid employs such solvents, under conditions which limit amide formation by the solvent and thus increase the efficiency of acetic acid recovery. Methods for the direct extraction of acetic acid and the extractive fermentation of acetic acid also employ the modified solvents and increase efficiency of acetic acid production. Such increases in efficiency are also obtained where the energy source for the microbial fermentation contains carbon dioxide and the method includes a carbon dioxide stripping step prior to extraction of acetic acid in solvent.

34 Claims, 4 Drawing Sheets

MICROBIAL PROCESS FOR THE PREPARATION OF ACETIC ACID AS WELL AS SOLVENT FOR ITS EXTRACTION FROM THE FERMENTATION BROTH

Matter enclosed in heavy brackets [ ] appears in the original patent but forms no part of this reissue specification; matter printed in italics indicates the additions made by reissue.

CROSS-REFERENCE TO RELATED APPLICATIONS

This is a 371 of PCT/US99/20416, which claims the benefit of the priorities of U.S. patent application Ser. No. 60/099,438, filed Sep. 8, 1998; U.S. patent application Ser. No. 60/099,439, filed Sep. 8, 1998; U.S. patent application Ser. No. 60/099,440, filed Sep. 8, 1998; and U.S. patent application Ser. No. 60/099,475, filed Sep. 8, 1998.

This invention has been partially supported by grants from the United States Department of Energy, Cooperative Agreement No. DE-FC02-90CE40939. The United States government has an interest in this invention.

FIELD OF THE INVENTION

The present invention relates generally to improved methods for the microbial production of acetic acid. More particularly, the invention relates to extraction of acetic acid from aqueous streams, and from the microbial fermentation of desirable chemical products from gaseous streams, such as waste gas streams, industrial gas streams, or from gas streams produced from the gasification of carbonaceous materials.

BACKGROUND OF THE INVENTION

Methods for the anaerobic fermentation of carbon monoxide, and/or hydrogen and carbon dioxide to produce acetic acid, acetate salts or other products of commercial interest, such as ethanol, have been performed at laboratory bench scale. See, e.g., Vega et al, (1989) Biotech. Bioeng., 34:785–793; Klasson et al (1990) Appl. Biochem. Biotech., 24/25: 1; Vega et al (1989) Appl. Biochem. Biotech., 20/21: 781–797; and Klasson et al (1992) Enz. Microbio. Tech., 19: 602–608, among others. More recently, the present inventors have discussed large-scale methods for the fermentation of industrial gas streams, particularly waste gas streams, into products of commercial use by using methods employing fermentation of the gas stream, an aqueous nutrient medium and an anaerobic bacteria or mixtures thereof in a bioreactor. See, e.g., U.S. Pat. Nos. 5,173,429; 5,593,886 and International Patent Publication No. WO98/00558, incorporated herein by reference.

According to the above-cited prior art of the inventors, one such large scale process involves the following summarized steps. Nutrients are continuously fed to a bioreactor or fermenter in which resides a culture, either single or mixed species, or anaerobic bacteria. A gas stream is continuously introduced into the bioreactor and retained in the bioreactor for sufficient time to maximize efficiency of the process. Exhaust gas containing inert and unreacted substrate gases, are then released. The liquid effluent is passed to a centrifuge, hollow fiber membrane, or other solid-liquid separation device to separate out microorganisms that are entrained. These microorganisms are returned to the bioreactor to maintain a high cell concentration which yields a faster reaction rate. Separation of the desired biologically produced product(s) from the permeate or centrifugate occurs by passing the permeate or centrifugate to an extractor where it is contacted with a solvent, such as a di-alkyl and tri-alkyl amine in a suitable cosolvent, or tributyl phosphate, ethyl acetate, tri-octyl phosphine oxide and related compounds in a co-solvent. Suitable cosolvents include long chain alcohols, hexane, cyclohexane, chloroform, and tetracholoroethylene.

The nutrients and materials in the aqueous phase passes back to the bioreactor and the solvent/acid/water solution passes to a distillation column, where this solution is heated to a sufficient temperature to separate the acid and water from the solvent. The solvent passes from the distillation column through a cooling chamber to lower the temperature to the optimum temperature for extraction, then back to the extractor for reuse. The acid and water solution passes to a final distillation column where the desired end product is separated from the water and removed. The water is recirculated for nutrient preparation.

Further, a variety of acetogenic bacteria are well known to produce acetic acid and other commercially interesting products when subjected to such fermentation processes, including novel strains of Clostridium ljungdahlii [See e.g., U.S. Pat. Nos. 5,173,429 and 5,593,886 and International Patent Publication No. WO98/00558].

Despite such knowledge and advances in the art of microbial fermentation of a variety of gas streams, acetic acid production is limited by the acetic acid loading potential of the solvent used, and by the degradation of the solvent as it travels through the production process, among other issues. In view of the ever-increasing need to produce acetic acid, as well as to convert industrial waste gases into useful non-polluting products, there remains a need in the art for processes which are more efficient in producing the desired commercial product and compositions which can enhance performance of such methods.

SUMMARY OF THE INVENTION

In one aspect, the present invention provides a modified water-immiscible solvent useful in the extraction of acetic acid from aqueous streams comprising a substantially pure mixture of isomers of highly branched di-alkyl (or secondary) amines. This solvent can extract the acid in the absence of a co-solvent. In a preferred embodiment, this solvent is a modified form of Adogen283® solvent [Witco Corp.] which is substantially reduced in its content of alcohols and monoalkyl (or primary) amines. In another preferred embodiment, the solvent is further reduced in content (i.e. substantially purified) or tri-alkyl (or tertiary) amines.

In another aspect, the invention provides a method for treating a solvent comprising alcohols, monoalkyl amines, a mixtures of isomers of highly branched di-alkyl amines and tri-alkyl amines to improve its acetic acid extractive capacity comprising distilling from the solvent substantially all the alcohols and monoalkyl amines. In another embodiment, the method involves subjecting the distilled solvent to a second distillation to remove substantially all tri-alkyl amines.

In yet a further aspect, the invention provides a novel water-immiscible solvent/co-solvent mixture useful for the extraction of acetic acid, preferably at concentrations less than 10%, from an aqueous stream comprising an above-described modified water-immiscible solvent useful in the extraction of acetic acid from aqueous streams comprising a substantially pure mixture of isomers of highly branched di-alkyl amines and a selected cosolvent. In a preferred embodiment, the cosolvent is a low boiling hydrocarbon having from 9 to 11 carbon atoms, which hydrocarbons forms an azeotrope with water and acetic acid.

In still another aspect, the invention provides a non-fermenting process for obtaining acetic acid from an aqueous stream comprising contacting the stream with a modified solvent/cosolvent mixture as described above; extracting the acetic acid from the aqueous phase into the solvent phase; and distilling the acetic acid from its admixture with the solvent under a temperature not exceeding 160° C.

In yet a further aspect, the invention provides a non-fermenting process for obtaining acetic acid from an aqueous stream comprising contacting the stream with a solvent/cosolvent mixture as described above; extracting the acetic acid from the aqueous phase into the solvent/cosolvent phase; and distilling the acetic acid from its admixture with the solvent/cosolvent under a temperature not exceeding 160° C. under a vacuum.

In a further aspect, the present invention provides an anaerobic microbial fermentation process for the production of acetic acid, the process comprising the steps of (a) fermenting in a bioreactor an aqueous stream comprising a gas selected from the group consisting of carbon monoxide, carbon monoxide and hydrogen, hydrogen and carbon dioxide, and carbon monoxide, carbon dioxide and hydrogen, in a nutrient mixture with an anaerobic acetogenic bacterium, thereby producing a broth comprising acetic acid; (b) continuously extracting acetic acid from the broth with a modified solvent/cosolvent mixture as described above; (c) continuously distilling from the product of (b) the acetic acid separately from the solvent at a temperature not exceeding 160° C., and (d) optionally recycling the solvent and the broth through the bioreactor. The extracting and distilling steps occur without substantially degrading the amine to an amide, thus enhancing the efficiency of acetic acid recovery from the broth.

In still another aspect, the present invention provides a method for enhancing the recovery of acetic acid from a fermentation broth comprising an aqueous stream containing one or more of carbon monoxide, carbon dioxide and hydrogen, and an anaerobic acetogenic bacterium, and nutrient medium, the method comprising contacting the stream with a solvent comprising the above-described modified di-alkyl amine and a selected co-solvent; continuously extracting the acetic acid from the stream in the solvent mixture, and distilling acetic acid from the solvent mixture, under a vacuum at a distillation temperature of below 160° C. therefrom, without substantially degrading the amine to amide.

In still another aspect, the invention provides an improved method for enhancing the recovery of acetic acid from anaerobic microbial fermentation of an aqueous stream comprising carbon monoxide, carbon monoxide and hydrogen, carbon monoxide, carbon dioxide and hydrogen, or carbon dioxide and hydrogen, wherein the method comprises the steps of contacting the fermentation product of the stream with a water-immiscible solvent, extracting the fermentation product from the stream, and distilling acetic acid therefrom. The improvement comprises employing as the solvent the modified solvent/cosolvent mixture described above and performing the distillation step at a temperature not exceeding 160° C. without substantially degrading the amine to amide.

In yet a further aspect, the invention provides an anaerobic microbial fermentation process (i.e., an extractive fermentation process) for the production of acetic acid which is accomplished without filtration or cell separation occurring prior to extraction. In one embodiment, this method involves providing in a fermenter an anaerobic acetogenic bacterium in a nutrient mixture and a modified water-immiscible solvent comprising a substantially pure mixture of isomers of highly branched di-alkyl amines with a selected cosolvent, for a time sufficient to acclimate the bacteria to the solvent. Into the fermenter is introduced a gas stream comprising one or more of carbon dioxide, carbon monoxide and hydrogen and a fermentation broth comprising the bacteria, nutrient medium, acetic acid, solvent mixture and water. The fermentation broth containing the cells and solvent mixture is introduced into a settling tank, wherein an aqueous phase containing the bacteria and nutrient medium settles to the bottom of the tank from the solvent phase which contains acetic acid, solvent and water, without filtration. Continuous distillation under a temperature not exceeding 160° C. removes the acetic acid separately from the solvent. The distilling step occurs without substantially degrading the amine to an amide, thus enhancing the efficiency of acetic acid recovery from the broth.

In still another aspect, the invention provides an anaerobic microbial fermentation process (i.e., a direct contact extraction process) for the production of acetic acid, which involves no filtration of bacterial cells. The process comprises the steps of: (a) fermenting in a bioreactor an aqueous stream comprising a gas containing one or more of carbon monoxide, carbon dioxide and hydrogen in a nutrient mixture with an anaerobic acetogenic bacteria, thereby producing a broth comprising acetic acid, water, and bacterial cells; (b) introducing into a conventional extraction device, such as a column with either solvent or water as the continuous phase (i) the broth with no cell separation and (ii) a solvent mixture comprising a modified water-immiscible solvent useful in the extraction of acetic acid from aqueous streams comprising a substantially pure mixture of isomers of highly branched di-alkyl amines and a selected co-solvent, wherein a solvent phase containing acetic acid, solvent and water exits the column separately from an aqueous phase comprising the bacteria and nutrient media; and (c) continuously distilling from the solvent phase of (b) the acetic acid separately from the solvent at a temperature not exceeding 160° C. The steps (b) and (c) occur without substantially degrading the amine to an amide, thus enhancing the efficiency of acetic acid recovery from the broth.

In still another aspect, the invention provides an anaerobic microbial fermentation process for the production of acetic acid which comprises the step(s) of removing dissolved carbon dioxide, and optionally dissolved hydrogen sulfide, from the fermentation broth before extraction. The steps of this process can include (a) fermenting in a bioreactor a gas stream comprising one or more of carbon monoxide, carbon dioxide and hydrogen in a nutrient mixture with an anaerobic acetogenic bacteria, thereby producing a fermentation broth comprising acetic acid and dissolved carbon dioxide; (b) removing the carbon dioxide from the fermentation broth prior to extraction; (c) contacting the broth (b) with a solvent containing a di-alkyl amine, preferably the modified solvent/cosolvent mixture of this invention for a time sufficient to cause the formation of a solvent phase containing acetic acid, the solvent and water: and (d) continuously distilling acetic acid from the solvent phase. The carbon dioxide/hydrogen sulfide removal step may be accomplished with a stripping gas, by preheating the broth or by reducing the fermentation broth pressure rapidly.

Other aspects and advantages of the present invention are described further in the following detailed description of the preferred embodiments thereof.

DETAILED DESCRIPTION OF THE INVENTION

Figure 1:
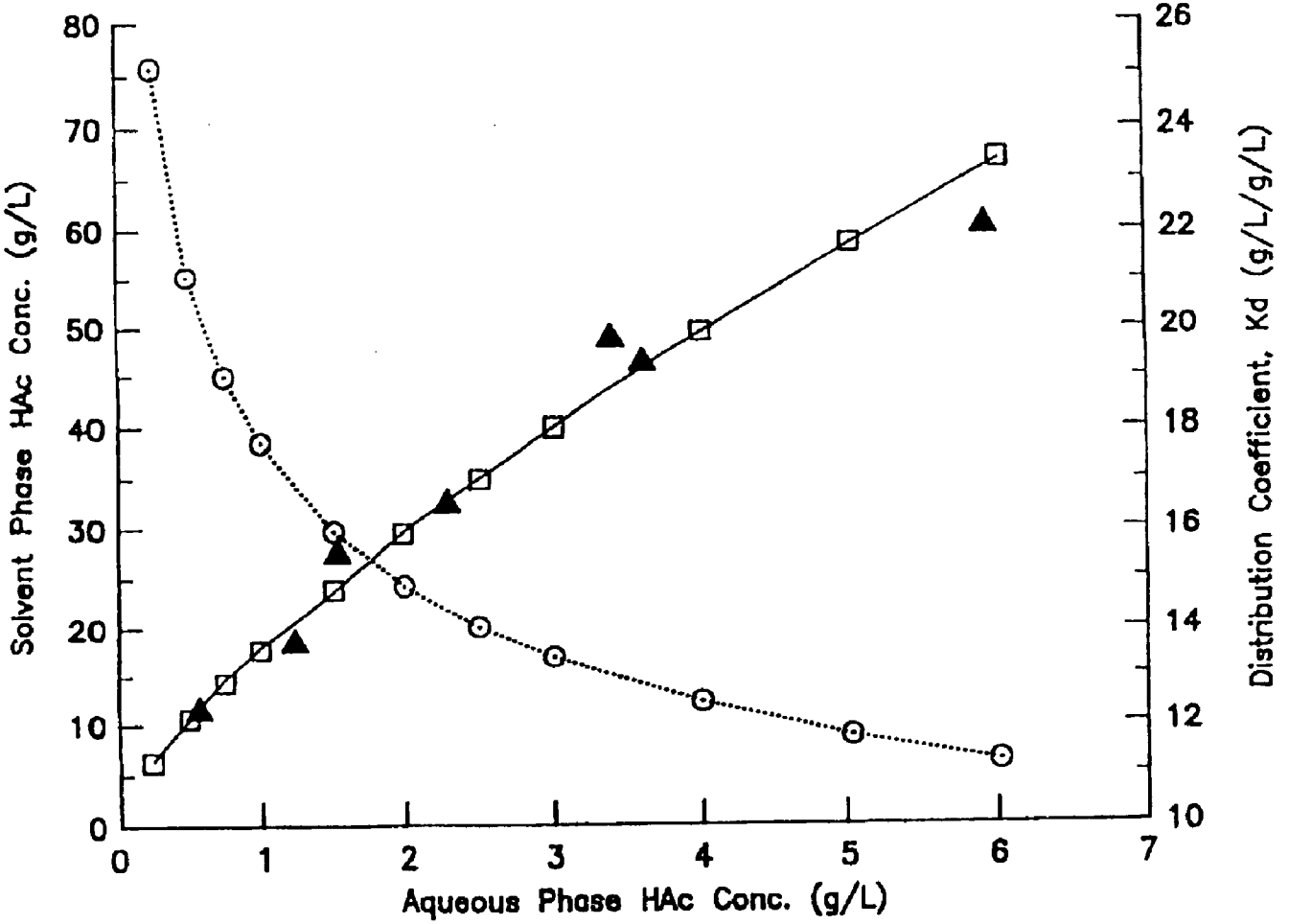
FIG. 1 is a graph charting solvent phase acetic acid (HAc) concentration in g/L vs. aqueous phase HAc concentration in g/L for acetic acid recovery processes employing 60% of the modified solvent. Adogen283®LA in an azeotroping solvent. SX-18. Experimental points are represented by triangles theoretical points by squares and coefficients of extraction ($K_d$) by circles.
Figure 2:
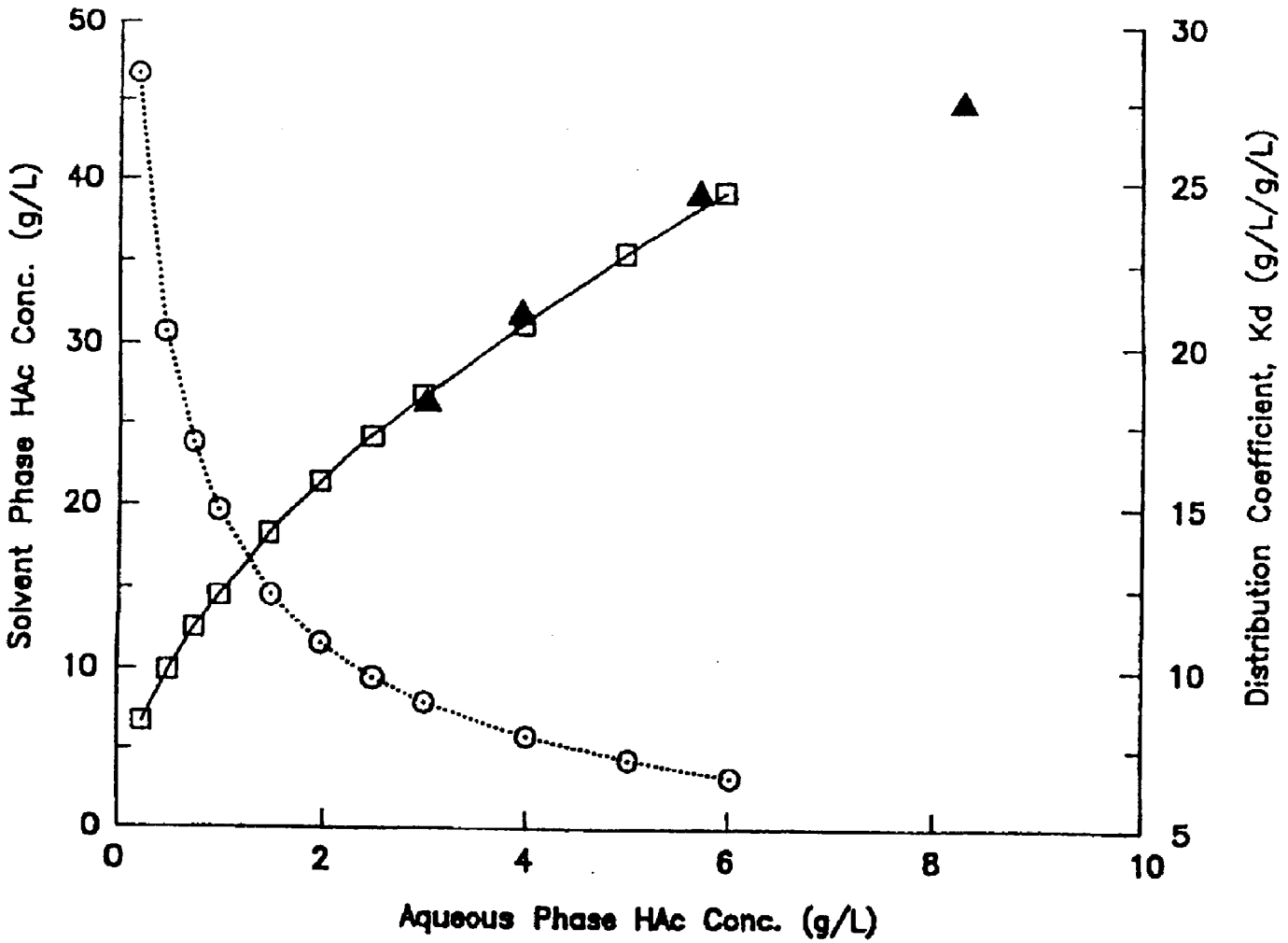
FIG. 2 is a similar graph, except that the solvent mixture is 33% modified solvent in cosolvent.

The compositions and processes of the present invention are directed towards the improvement of processes for obtaining acetic acid from aqueous phases, including aqueous phases formed by fermentation processes. Thus, in one embodiment, the acetic acid recovery processes of the prior art are improved and recovery of acetic acid from dilute aqueous streams is enhanced by employing in an extraction and distillation process a solvent comprising a mixture of highly branched di-alkyl amines, and preferably a mixture of that solvent with a selected cosolvent in which limited solvent degradation occurs. In another embodiment, use of the same modified solvent/cosolvent mixture can enhance acetic acid recovery from a microbial fermentation process for gaseous streams which include extraction/distillation steps.

Other improvements in acetic acid recovery, from conventional fermentation processes provided by this invention involve eliminating the requirement for the separation of bacteria cells from the acetic acid-containing broth in the process and/or replacing the use of an expensive extractor, by directly contacting the bacterial cells with the selected modified solvent/cosolvent mixture.

Still other improvements in the efficiency of acetic acid recovery from conventional fermentation processes as well as the processes described below include removing dissolved carbon dioxide and optionally hydrogen sulfide from the fermentation broth prior to extraction.

A. The Modified Solvent and Solvent/Co-solvent Mixture

This invention provides a modified solvent and a solvent/co-solvent mixture which display highly desirable characteristics for extraction of acetic acid from aqueous phases containing the acid. This solvent and solvent mixture are useful for both extraction of acetic acid in non-fermenting processes as well as for extraction and distillation from a fermentation broth including an anaerobic acetogenic microorganism, aqueous nutrient medium, and energy and carbon sources from gas streams.

The desired solvent (for shorthand purposes, the "modified solvent") of this invention is defined as a water-immiscible solvent useful in the extraction of acetic acid from aqueous streams comprising a substantially pure mixture of isomers of highly branched di-alkyl mines. Such a modified solvent preferably has a coefficient of distribution ($K_d$) of greater than 10, and more preferably greater than 15. This solvent can extract acetic acid in the absence of a co-solvent.

By the term "substantially pure" is meant that the solvent contains greater than 50% by volume di-alkyl amines, and has as small a percentage as possible of monoalkyl amines. More preferably, the solvent contains greater than 70% di-alkyl amines. In another preferred embodiment, the solvent contains greater than 80% di-alkyl amines. In still a more preferred embodiment, the solvent contains between 80 to 100% di-alkyl amines. Such a substantially pure mixture further contains a percentage of mono-alkyl amines in the solvent which can range between 0.01% to about 20% by volume. More specifically, the monoalkyl amine content can range from less than 1% to about 10%. In some embodiments, the mono-alkyl amine percentage ranges from about 5% to about 15%. In still other embodiments of this invention, the solvent contains less than 5% and preferably less than 1% by volume mono-alkyl amines. Another embodiment of such a modified solvent is one that has an amount of tri-alkyl amines that is less than a maximum of 50% by volume, and preferably as low as 0% tri-alkyl amines. In some embodiments, the amount of tri-alkyl amines in the solvent is less than 40% by volume. Still another embodiment contains less than 25% by volume tri-alkyl amines. A preferred embodiment contains less than 10% by volume tri-alkyl amines, and preferably less than 5% by volume tri-alkyl amines. Still a preferred embodiment contains less than about 1% by volume tri-alkyl amines. Still other solvents of this invention contain optionally as small a percentage as possible of alcohols, desirably less than 25% by volume to about 0%. Another embodiment contains less than 10% by volume alcohol, desirably less than 5% by volume and preferably less than 1% by volume alcohol.

For example, one desirable modified solvent contains about 90% of a mixture of isomers of highly branched di-alkyl amines and about 10% of tri-alkyl amines. Thus, useful modified solvents may have small amounts of the alcohol, monoalkyl amines and trialkyl amines, and still increase the efficiency of the acetic acid production in the methods of this invention.

One embodiment of a modified solvent as described above may be prepared by modification of a commercial solvent, i.e., removing alcohols and monoalkyl amines to create a desirable modified solvent for the processes of the present invention as described above. The commercial product Adogen283® solvent (Witco Corporation) is a di-alkyl amine, i.e., di(tridecyl)amine or N-tridecyl-1-tridecanamine (CAS No. 5910-75-8 or 68513-50-8). Essentially Adogen283® solvent is a complex mixture of isomers which can be classified as monoalkyl, di-alkyl and tri-alkyl amines. The unmodified Adogen283® solvent has an average molecular weight of 395, and a total amine value of 144.0, and contains, for example, 0.29 percent alcohols, 5.78 percent mono-alkyl amine, and 85.99 percent di-alkyl amine. Mass spectrometry analysis of the higher boiling amines of Adogen283® solvent is indicated below in Table 1.

TABLE I

| Amine Formulae | Amine Type | Molecular Wt | Mole Percent |
|---|---|---|---|
| $(C_{13}H_{27})_2NH$ | Di-alkyl | 381 | 54 |
| $(C_{13}H_{27})(C_{12}H_{25})NH$ | Di-alkyl | 367 | 27 |
| $(C_{13}H_{27})(C_{14}H_{29})NH$ | Di-alkyl | 395 | 10 |
| $(C_{13}H_{27})_3N$ | Tri-alkyl | 563 | 5 |
| $(C_{13}H_{27})_2(C_{12}H_{25})N$ | Tri-alkyl | 549 | 4 |

Although this commercial Adogen283® solvent is recognized as a useful extraction solvent for extracting dilute acetic acid from aqueous phases, until the present invention, the art recognized that when Adogen283® solvent was distilled, it would degrade substantially, i.e., about 40% converted to unwanted amides by reaction of the amine with acetic acid over a period of 3 hours under distillation conditions [J. W. Althouse and L. L. Tazlarides, J. Indus. Eng. Chem. Res., 31 1971–1981 (1992)], thereby making it undesirable for acetic acid recovery processes involving distillation. According to the above report, the alcohols is Adogen283® solvent also can react with acetic acid at distillation temperatures to form esters. Further, an Adogen283® solvent or modifications thereof, even in combination with a co-solvent, has previously been rejected for processes involving distillation, because of its undesirable amide formation [N. L. Ricker el al, J. Separation Technol., 1:36–41 (1979)].

Thus, a key aspect of the present invention was the determination by the inventors of a method for modifying a solvent, such as Adogen 283® solvent, having a high coefficient of distribution (e.g., $K_d$ greater than or equal to 5, and preferably between about 10 to 20) to eliminate its unwanted characteristics. A further aspect of this invention is the combination of the modified solvent with a selected cosolvent, to make a suitable solvent mixture for acetic acid recovery processes involving distillation. The modification of Adogen283 ® solvent to substantially remove or reduce the percentages of alcohols and monoalkyl amines is accomplished as follows. The commercial solvent is subjected to distillation, preferably in a wiped-film evaporator; and the distilled solvent is then subjected to an acid wash step. The acid wash step is accomplished at ambient temperature, preferably using a dilute organic acid at a pH of less than 5. One exemplary acid is dilute acetic acid (at about 1–50 g/L, preferably less than 30 g/L and more preferably less than 3 g/L. The acid is generally used at a ratio of dilute acid to solvent of at least 1:1. A preferred ratio is about 5:1 acid to solvent. These two steps of distillation and acid washing remove low boiling organic materials and mono-alkyl amines. Preferably by "low boiling" is meant below about 115° C., preferably below about 100° C., of about 70 torr.

In one specific example, the distillation was performed in a laboratory wiped-film evaporator, with a feed rate of 56.4 g Adogen283® solvent/hour, a temperature of 164.3° C., and a pressure of 69.9 torr. The alcohols and monoalkyl amines separate out and are removed at the top of the distillation column by this process, leaving the resulting modified solvent containing a mixture of highly branched di-alkyl amines and tri-alkyl amines to be removed at the bottom of the distillation column. This modified solvent was referred to as Modified Solvent A.

Modified Solvent A was characterized by containing 0.02 percent low boiling organic materials, 0.16 percent mono-alkyl amine, 90.78 percent di-alkyl amine and 9.04 percent tri-alkyl amine. Table II provides a comparison of the fractions (in percentages) which make up the unmodified Adogen283® solvent, the Modified Solvent A, and the fractions removed as a result of the above-described process:

TABLE II

| Fractions | Unmodified Adogen283 ® Solvent | Modified Solvent A | Removed Distillate |
|---|---|---|---|
| Low boiling organic materials | 0.29% | 0.02% | 3.06% |
| Mono-alkyl Amines | 5.78% | 0.16% | 53.36% |
| Di-alkyl Amines | 85.99% | 90.78% | 43.59% |
| Tri-alkyl Amines | 7.95% | 9.04% | 0% |
| Total Weight | 218.91 g | 195.96 g | 22.95 g |

This more preferred Modified Solvent A has an extraction coefficient of about 10 or higher, and contains among other components a mixture of isomers of highly branched di-alkyl amines, modified to substantially reduce the alcohol content and the amount of mono-alkyl amines therefrom. The Modified Solvent A is an excellent acetic acid concentrating solvent, particularly for use in the methods of this invention. The coefficient of extraction of this modified solvent increases as the concentration of acetic acid decreases.

Modified Solvent A may then be further purified to provide yet another desirable modified solvent, referred to as Modified Solvent B. Modified Solvent A is introduced into another distillation column under the same conditions as above. This distillation enables the di-alkyl amines in Modified Solvent A to be distilled and removed at the top of the distillation column, resulting in Modified Solvent B, while the tri-alkyl amines are removed at the bottom of the column. Modified Solvent B is characterized by a slightly better coefficient of extraction (greater than 10) and even better performance in the methods of this invention when combined with a selected cosolvent.

Based on the disclosures herein relating to the modification of commercial Adogen283® solvent and the Modified Solvents A and B, it is anticipated that other conventional solvents containing isomeric mixtures of highly branched di-alkyl amines, with some tri-alkyl amines, along with monoalkyl amines, alcohols and other components, such as Amberlite LA-2 MW=375 [Rohm & Haas] and others mentioned in H. Reisinger and C. J. King, Ind. Eng. Chem. Res., 34:845–852 (1995), may be similarly treated to substantially remove alcohols mono-alkyl amines, and where desired, tri-alkyl amines, as described herein to create suitable modified solvents for use in processes involving extraction and distillation of acids from aqueous phases. One of skill in the art can readily apply this teaching to such other solvents without undue experimentation.

Another aspect of this invention involves a mixture of a modified solvent of this invention with a selected cosolvent, which mixture also has preferred characteristics for use in extraction and distillation processes for the recovery of acetic acid. A wide variety of non-alcohol cosolvents may be selected for admixture with the modified solvents identified above, as well as with the commercially available Adogen283® solvent. Because of the high distribution coefficient that is possible with the use of Adogen 283® solvent and modified versions thereof, a wide variety of co-solvents may be employed in these admixtures. The cosolvent merely decreases the $K_d$ in proportion to the fraction of cosolvent employed in the mixture. As an example, a mixture of 50% Adogen 283® solvent or a modified version thereof and 50% cosolvent of any type has one half of the $K_d$ of pure Adogen 283® solvent. While this phenomenon is true with other amine based solvents, e.g., Alamine 336®solvent, Adogen 381® solvent, Adogen 260® solvent, among others), the values of $K_d$ for these latter pure solvents are very low (1 to 3), so the dilution with cosolvents results in uneconomically low $K_d$ values (0.5 to 1.5 lower). In using other solvents, such as the commercially available, Alamine 336®solvent, Adogen 381® solvent, etc., the cosolvent must be chosen carefully to enhance the distribution coefficient.

Although the $K_d$ is dependent on the acid concentration in the fermenter (normally about 3–6 g/L), the desired $K_d$ of the solvent mixture is desirably between about 1 and 20. For an acid concentration of about 4.5–5.5 g/L, the $K_d$ of the solvent mixture is desirably between about 8–11. Still another $K_d$ of the solvent mixture is about 6–20. However, other values for the coefficient may be used in the practice of this invention.

The solvent/co-solvent mixture must be immiscible with water and readily separate from water at reduced temperatures. The selected cosolvent must have a boiling point lower than that of the commercial solvent or modified solvents described above. For example, a preferred co-solvent boils between 125° C. and 250° C. More preferably the cosolvent boils at between about 150° C. and 200° C. In one embodiment, the cosolvent boils at about 165° C. Alcohols are to be avoided in selection of a cosolvent because they react with acetic acid to form esters, and also cause emulsification. The selected cosolvent can improve physical properties such as viscosity of the mixture and can also aid in the reduction of the boiling point of the solvent. The selection of suitable cosolvents can be made by one of skill in the art, further taking into account that low toxicity cosolvents are essential for any water solubility and return to the fermenter, and where the cosolvent will come into contact with the bacteria. Obviously, the selected cosolvent must be able to be tolerated by the bacteria.

A preferred co-solvent for use in the solvent mixture of this invention is one that forms an azeotrope (i.e., a mixture that is not easily separated and behaves "as one") with water and acetic acid when in the vapor form. The azeotroping cosolvent enhances the volatility of at least one of the components, e.g., water. The formation of an azeotrope permits the cosolvent and the water/acetic acid as vapor to move together (essentially as one) up and out the top of a distillation column. When the vapor is condensed, the cosolvent and the acetic acid/water separate. In the distillation processes described below, this permits the cosolvent to be decanted and returned to the first distillation column. The acetic acid and water (and some residual cosolvent) can then go onto a second distillation column for acetic acid recovery. The primary advantage of an azeotroping cosolvent is that it permits acetic acid recovery in two distillation columns rather than the three required for non-azeotroping cosolvents.

Some cosolvents displaying the required characteristics include low-boiling point hydrocarbon co-solvents that form azeotropes with acetic acid. Particularly desirable cosolvents fitting this description include alkanes, particularly those in the range of C-9 to C-11. Among such useful co-solvents are n-nonane, n-decane, n-undecane, ethers, and Orfom® SX-18™ solvent (Phillips Mining, Inc.), i.e., which is a mixture of C9–C11 isoalkanes. Still other cosolvents useful for mixture with the modified solvents of this invention include those non-alcohol solvents, among others listed in Table 3, page 1976 of Althouse (1992), cited above and incorporated herein by reference.

Such co-solvents, when admixed with a modified di-alkyl amine solvent as described above, can reduce the boiling point of the solvent system, particularly when the solvent system is distilled under vacuum. The reduced boiling temperature also prevents or limits amide formation from the di-alkyl amine. Such a solvent/azeotroping co-solvent mixture permits the distillation process to be carried out in two columns. Generally, the amount of modified solvent in the solvent/cosolvent mixture can range in the mixture from about 10 to about 90% by volume. Desirably, the amount of modified, di-alkyl amine-containing solvent of this invention is between about 30 to about 70% by volume of the solvent/cosolvent mixture. In preferred embodiments, the modified solvent is present in the mixture at about 60% by volume. At least 10% of cosolvent is necessary to form a modified solvent/cosolvent mixture of this invention. The amount of cosolvent can range from about 10 to about 90%; more desirably from about 30 to 70% by volume. In preferred embodiments, the modified solvent is present in the mixture at about 40% by volume. Thus one preferred and exemplary solvent/cosolvent mixture of the present invention comprises 60% Modified Solvent A and 40% Orfom® SX18 solvent.

One of skill in the art is expected to be able to adjust the percentages of modified solvent and cosolvent as desired for any particular distillation apparatus or process. Adjustments to the proportion of modified solvent to cosolvent to prepare a desired mixture will be based on factors such as the identity and contents of the modified solvent and cosolvent, their relative distribution coefficients, their viscosities, as well as practical considerations, such as the availability of heat, the size of the equipment, and the relative costs of the two solvent components. For example, the best extraction coefficient appears to correlate with a high amine content, which increases the expense of the solvent system. Thus for some uses the high expense would influence the desired proportions of the modified solvent/cosolvent. Also restricting the upper value of the modified solvent in the mixture is its viscosity and boiling point, both of which are reduced with the cosolvent.

As one example, the SX-18 co-solvent proportionally reduces the distribution coefficient of the modified solvent mixture (e.g., 50% Modified Solvent A in SX-18 solvent has one half the distribution coefficient of 100% Modified Solvent A), but is easier to work with because of lowered viscosity and increased ability to recover due to the presence of the co-solvent. The cosolvent SX-18 boils at between about 160–167° C. and therefore also lowers the boiling point of the mixture, thereby reducing amide formation. One of skill in the art is expected to have the ability to balance these factors to prepare any desired mixture of the modified solvent and cosolvent.

The desirable characteristics of the modified solvent/cosolvent mixtures of this invention particularly suit them for use in extraction and distillation processes for acetic acid. For extraction., the desirable properties of the solvent mixture of this invention include a high coefficient of extraction (i.e., about 3 or more, and preferably about 10 or more), immiscibility in water, good water/solvent separation, low toxicity to bacterial culture, a clear difference in viscosity and density from that of water, and good selectivity for acetic acid over other products of fermentation, such as ethanol, salts, and water. For distillation, the desirable properties of the solvent and solvent mixture of this invention include, for example, a distinct boiling point difference between the acetic acid (i.e., 118° C.) and co-solvent (e.g., 165° C.). These differences are also useful in performance of the processes of this invention, because the greater the differences between the boiling points of these components, the smaller can be the distillation column, resulting in efficiency and cost improvements in the acetic acid recovery processes.

Significantly, use of the modified solvent/cosolvent mixtures of this invention involve only negligible solvent losses due to thermal or reactive degradation, e.g., oxidation. See, e.g., FIG. 4 and Example 2. The solvent and cosolvent also are characterized by limited reactivity with the acetic acid, media components, biomaterials, and other unknowns in the aqueous phase or broth and low miscibility in water. Desirably, the processes of this invention for using the solvent/cosolvent reduces or substantially eliminates any tendency for acetic acid and the solvent/cosolvent to form unwanted byproducts, such as amides, which could be formed from a reaction involving the amines in the novel modified solvent and solvent mixtures of this invention.

It is expected that one of skill in the art will readily be able to modify the solvent/cosolvent mixture of this invention in light of the teachings of this specification and with regard to knowledge available as to the above-noted factors. Such modifications are believed to be encompassed by the scope of the appended claims.

B. Use of Novel Solvent/Co-solvent Mixtures in Recovering Acetic Acid

The methods of this invention employ the modified solvent/co-solvent mixtures described above and particular process steps to avoid formation of unwanted amides. The use of the modified solvent/cosolvent mixtures permit improved recovery of acetic acid from aqueous phases, in either non-fermentation processes of microbial fermentation processes.

Thus according to one embodiment of this invention, a non-fermenting process for obtaining acetic acid from an aqueous phase may employ the modified solvent/cosolvent mixtures described above. Such a process employs as a first step continuously contacting the aqueous phase with a solvent mixture comprising a modified di-alkyl amine solvent/cosolvent mixture as described above, to permit the acetic acid from the aqueous phase to be extracted into the solvent phase. This step may employ conventional extraction devices, such as columns, mixing and settling tanks and similar apparatus designed for extraction and well-known to the art. Additionally, extraction conditions may be optimized also be resorting to teachings in the art. The extraction temperature is desirably ambient temperature, i.e., about 20° C. to about 80° C. At about 80° C., any carbon dioxide is essentially all relieved from the solvent, but extraction is still efficient.

Thereafter, the acetic acid is distilled from the solvent phase under a distillation temperature which reduces the conversion of the amines in the solvent to amides. The distillation temperature as used herein means the temperature at the bottom of column. According to the present invention, the distillation temperature may range from about 115° C. to about 160° C. to reduce amide formation. Most significantly, the processes of this invention require the distillation temperatures to be below 130° C. to limit amide formation, while permitting acetic acid recovery.

In a preferred embodiment, the distillation step is performed under an oxygen-free vacuum, which also serves to reduce the temperature to minimize amide formation and oxidative degradation of the solvent or solvent/cosolvent mixture. The higher the vacuum (i.e., lower absolute pressure) the lower the temperature and the less amide formation and oxidative degradation. Desirably a vacuum of less than 10 psia is required for this step. Preferably, the vacuum is selected from between about 0.1 psia and 5 psia for the distillation step. More preferably, a vacuum of 4 psia or less is useful in this distillation step to enhance recovery of the acetic acid. As yet a further advantage of the use of the modified solvent/azeotroping cosolvent mixture of this invention is the use of two distillation columns to enhance the efficiency of recovery of acetic acid from aqueous phases in comparison to processes of the prior art.

The control of distillation temperature in the processes of this invention to limit solvent degradation may be accomplished by a combination of factors, such as selection of the cosolvent, ratio of solvent to cosolvent and conditions of vacuum for the distillation step. Given the teachings of this specification, one of skill in the art may select the appropriate combination of factors to control the distillation temperature as required. For example, one of skill in the art may readily adjust the temperature and vacuum conditions of the distillation step within the above ranges to achieve a desired efficiency of acetic acid recovery while minimizing amide formation and oxidative degradation of the solvent according to this invention. Such modifications are encompassed within the appended claims.

According to yet another embodiment of this invention, an anaerobic microbial fermentation process for the production of acetic acid employs the modified solvent/cosolvent mixture of this invention to enhance the efficiency of recovery of acetic acid. In this process, a fermentation broth containing, among other components, acetic acid, is formed by fermenting in a bioreactor with an anaerobic acetogenic microorganism, an aqueous stream comprising a source of nutrients, and a gas containing various mixtures of carbon monoxide, or carbon dioxide or hydrogen. Thus, in one embodiment, the gas stream contains carbon monoxide. In another embodiment the gas stream contains carbon dioxide and hydrogen. In still another embodiment the gas stream contains carbon dioxide, carbon monoxide and hydrogen. In yet another embodiment the gas stream contains carbon monoxide and hydrogen. Such gases may desirably be obtained from waste gases of various industrial processes.

Also, as mentioned, in the fermentation broth is an anaerobic acetogenic bacterium and a nutrient medium necessary for growth of the bacterium. The anaerobic bacteria may be one strain of bacteria or a mixed culture containing two or more of acetogenic bacteria, including, without limitation, Acetobacterium kivui, A woodii, Butyribacterium methylotrophicum, Clostridium aceticum, C. acetobutylicum, C. formoaceticum, C. kluyveri, C. thermoaceticum, C. thermocellum, C. thermohydrosulfuricum, C. thermosaccharolyticum, Eubacterium limosum, Peptostreptococcus productus, and C. ljutigdahlii, and mixture thereof. Particularly desirable acetogenic bacteria are those strains previously discovered by the inventors, namely, C. ljutngdahlii strain PETC ATCC 49587, strain O-52 ATCC 55989 deposited on Jun. 27, 1997, strain ER12 ATCC 55380 deposited on Dec. 8, 1992 and strain C-01 ATCC 55988 deposited on Jun. 27, 1997, and mixtures thereof. These acetogenic bacteria are generally available from depositories such as the American Type Culture Collection, 10801 University Boulevard, Manassas, Va. 20110-2209 or from commercial or educational institutions. The above-identified microorganisms are deposited pursuant to the Budapest Treaty for the Deposit of Microorganisms for Patent Purposes, and such deposits comply with all the requirements thereof.

Nutrients are continuously fed to the fermenter. The nutrient media useful in such fermentation broth are conventional and include those nutrients known to be essential for the growth of such acetogenic bacteria. An exemplary nutrient medium formation (Medium A plus Medium B) for the growth of acetogenic bacteria at atmospheric pressure, and which is sulfide based is illustrated in the following Table III. However, many different formulae of nutrient media may be used with components of differing concentrations. One of skill in the art can readily formulate other suitable nutrient media for the processes described herein. The formula of Table III is merely one suitable formulation.

TABLE III

| Component | Quantity per liter water |
|---|---|
| Medium A | |
| $Mg(CH_3COO)_2.4H_2O$ | 0.1452 g |
| $Ca(CH_3COO)_2.H_2O$ | 0.00677 g |
| $CH_3COOK$ | 0.5574 g |
| Nitrilotriacetic acid | 0.0141 g |
| 85% $H_3PO_4$ | 0.56 ml |
| $FeCl_2.4H_2O$ | 113 mg |
| $ZnSO_4.7H_2O$ | 5.6 mg |
| $MnCl_2.4H_2O$ | 1.7 mg |
| $H_3BO_5$ | 17 mg |
| $CoCl_3.6H_2O$ | 11 mg |
| $CuCl_2.H_2O$ | 1.1 mg |
| $NiCl_2.6H_2O$ | 2.3 mg |
| $Na_2SeO_3$ | 0.6 mg |
| Ca-D-Pantothenate | 0.846 mg |
| Thiamine | 0.706 mg |
| Biotin | 0.212 mg |
| Medium B | |
| $(NH_4)_2HPO_4$ | 1.2 g |
| $NH_4OH$ | 5.62 ml |
| $Na_2S.9H_2O$ | 1.251 mg |
| $NaMoO_4.2H_2O$ | 1.8 mg |
| $Na_2WO_4.2H_2O$ | 6.0 mg |

The selection of nutrients and other conditions for fermentation may be readily made by one of skill in the art with resort to existing knowledge, and depend on a variety of factors, such as the microorganism used, the size and type of the equipment, tanks and columns employed, the composition of the gas stream or energy source, etc. Such parameters may be readily selected by one of skill in the art in view of the teachings of this invention and are not a limitation of this invention.

As the fermentation occurs, exhaust gas containing inert and unreacted substrate gases, are released and the liquid fermentation broth or effluent is passed to a centrifuge, hollow fiber membrane, or other solid-liquid separation device to separate out microorganisms that are entrained and preferably return them to the fermenter.

Thereafter, the essentially cell-free aqueous stream from the fermentation broth (hereinafter "cell-free stream") is subjected to extraction with the modified solvent/cosolvent mixture in an extractor. The solvent to feed ratio (ratio of solvent volume to cell-free stream volume) can vary significantly from nearly zero to 10, for example. The lower the solvent to feed ratio, the higher the concentration of acid in the solvent and the lower the requirements for solvent. According to this invention, a solvent comprising a mixture of isomers of highly branched di-alkyl amines modified to remove mono-alkyl amines and a selected co-solvent, e.g., a low boiling hydrocarbon cosolvent mixture described above, is employed in the extraction step. As described in the above embodiment, this extraction is maintained at a temperature of between about 20° C. to about 80° C., depending on the viscosity of the solvent mixture. This extraction step removes the acetic acid from the cell-free stream and permits separation of the acetic acid from the nutrient media and other materials in the aqueous phase (which are recycled to the bioreactor) into a phase which includes the solvent, a very small amount of water and the acetic acid. Additionally, some components, such as Se, Mo, W and S from the medium are extracted into the solvent.

Still another step in the process involves continuously distilling the acetic acid and water component away from the extraction product's solvent and water. To accomplish this step, the solvent/acid/water solution passes to a first distillation column, where this solution is heated to a temperature which reduces the conversion of the amines in the solvent to amides. As described above, the distillation temperature must range between 115° C., to a maximum of about 160° C. to permit acetic acid recovery, while limiting solvent degradation and amide formation. Preferably, the temperature of the distillation step does not exceed about 130° C., in order to prevent amide formation. A key advantage of the present invention is that the extracting and distilling steps occur without substantially degrading the solvent amine to an amide, and thus enhances the efficiency of acetic acid recovery from the broth.

Where the solvent/co-solvent mixture of this invention employs an azeotroping cosolvent, the distillation columns used in the process operate more efficiently. The formation of an azeotrope permits the cosolvent and the acid/water to move together (essentially as one) up and out the top of the first distillation column during the distillation step. In the liquid form, the cosolvent and the acetic acid/water separate. Once separated, the cosolvent can be reintroduced into the distillation column. The acetic acid and water (and some residual cosolvent) then pass to a second distillation column where the cosolvent again forms an azeotrope with water and acid, and the three components flow as a vapor out the top of the column. The vapor is condensed and most of the liquid is refluxed. Because the condensed liquid contains a small amount of cosolvent, a small stream is continuously returned to the solvent distillation column. The product acetic acid is pulled out just above the first theoretical stage, i.e., the portion of the column where the solvent and acid separate.

A preferred embodiment of this method involves performing the distillation step under an oxygen-free vacuum, which also serves to reduce the temperature and avoid oxidative degradation of the solvent of solvent/cosolvent mixture. The higher the vacuum (i.e., lower absolute pressure) the lower the temperature and the less amide formation and oxidative degradation. As described above, the vacuum is preferably less than 10 psia. Desirably a vacuum of between about 0.1 psia and 5 psia is useful in the distillation step. More preferably, a vacuum of 4 psia or less is useful in this distillation step to further reduce the boiling point of the solvent/acid/water mixture, further reducing amide formation and enhancing recovery of the acetic acid. As yet a further advantage of the use of the modified solvent/azeotroping cosolvent mixture of this invention is the use of two distillation columns to accomplish enhanced recovery of acetic acid from aqueous phases in comparison to processes of the prior art.

The control of distillation temperature in the processes of this invention to limit solvent degradation may be accomplished by a combination of factors, such as selection of the cosolvent, ratio of solvent to cosolvent and conditions of vacuum for the distillation step. Given the teachings of this specification, one of skill in the art may select the appropriate combination of factors to control the distillation temperature as required. For example, one of skill in the art may readily adjust the temperature and vacuum conditions of the distillation step within the above ranges to achieve a desired efficiency of acetic acid recovery according to this invention. Such modifications are encompassed within the appended claims.

C. Extractive Fermentation and Direct Contact Extraction Method

According to yet another embodiment of this invention, the above-described novel modified solvent/cosolvent mixtures are useful in a process of "direct contact extraction" and "extractive fermentation", i.e., modifications of the anaerobic fermentation production process for the recovery of acetic acid described above. The modifications of the process allow the production of acetic acid via microbial fermentation without the need for bacterial cell separation prior to extraction or distillation. Further, these solvent mixtures when used in microbial fermentation of acetic acid can eliminate the need for use of a separate extractor. In addition to reducing the complexity of the process, this invention reduces the capital, operating and maintenance costs of the equipment needed to perform the process of producing acetic acid, as well as the time to obtain the product.

Thus, the "extractive fermentation" method of the invention provides an anaerobic microbial fermentation process for the production of acetic acid, which is a modification of the process described above. As a first step, the bioreactor or fermenter containing anaerobic acetogenic bacteria in a suitable nutrient mixture necessary for growth of the bacteria is contacted with the modified solvent/cosolvent mixture described above at about 37° C. and at least about one atmosphere of pressure (i.e., 14.7 psia) for a time sufficient to acclimate the bacteria to the presence of the solvent, i.e. to permit the bacteria to grow in the presence of the solvent. The anaerobic bacteria may be one strain of bacteria or a mixed culture containing two or more strains of acetogenic bacteria; the bacterial strains listed above in Part B may also be used in this modification of the invention. As many solvents are toxic to bacterial growth, this aspect of the invention involving direct contact between the bacteria and the solvent reflects the acclimation of the cells to solvent mixture, which is obtained by gradually increasing contact between the cells and solvent mixture over time.

Thereafter, an aqueous stream comprising a source of nutrients, and a gas containing various mixtures of carbon monoxide, or carbon dioxide or hydrogen, is introduced into the fermenter. Thus, in one embodiment, the gas stream contains carbon monoxide. In another embodiment the gas stream contains carbon dioxide and hydrogen. In still another embodiment the gas stream contains carbon dioxide, carbon monoxide and hydrogen. In yet another embodiment the gas stream contains carbon monoxide and hydrogen. As above, these gases may be obtained from industrial waste gases. According to this step, a fermentation broth containing, among other components, acetic acid, solvent, bacterial cells and water is formed.

Nutrients are continuously fed to the fermenter. The selection of the particular nutrients, media and other conditions of temperature and pressure, etc. for fermentation may be readily made by one of skill in the art given the teachings of this invention, and depend on a variety of factors, such as the microorganism used, the size and type of the equipment, tanks and columns employed, the composition of the gas stream or energy source, the gas retention time, and liquid retention time in the fermenter, etc. Such parameters may be readily balanced and adjusted by one of skill in the art and are not considered to be limitations on this invention.

As the fermentation occurs, exhaust gas containing inert and unreacted substrate gases, are released. Within the fermentation broth, the presence of the solvent continuously separates the acetic acid and a small amount of water into a lighter "solvent phase", from the heavier bacteria and nutrient medium and other heavier materials in the aqueous phase. The mixture of cell-free stream and solvent is continuously removed into a settling tank, where the lighter solvent phase is decanted from the heavier aqueous phase simply by the operation of gravity. No other solid-liquid separation methods are used. The heavier phase is recycled to the bioreactor/fermenter, and the lighter phase which includes the solvent, a small amount of water and the acetic acid solution passes to a first distillation column.

As described above, this solution is heated to a temperature for acetic acid recovery which minimizes the conversion of the amines in the solvent to amides. Preferably, the temperature of the distillation step does not exceed about 160° C., and more preferably 130° C., in order to prevent amide formation. A key advantage of the present invention is that the distilling steps occur without substantially degrading the solvent amine to an amide, and thus enhance the efficiently of acetic acid production.

Where the solvent/co-solvent mixture of this invention employs an azeotroping cosolvent, the distillation columns used in the process operate more efficiently. The formation of an azeotrope permits the cosolvent and the acid/water to move together (essentially as one) up and out the top of the first distillation column during the distillation step. In the liquid form, the cosolvent and the acetic acid/water separate. Once separated, the cosolvent can be reintroduced into the distillation column. The acetic acid and water (and some residual cosolvent) then pass to a second distillation column where the cosolvent again forms an azeotrope with water and acid, and the three components flow as a vapor out the top of the column. The vapor is condensed and most of the liquid is refluxed. Because the condensed liquid contains a small amount of cosolvent, a small stream is continuously returned to the solvent distillation column. The product acetic acid is pulled out just above the first theoretical stage.

A preferred embodiment of this method involves performing the distillation step under an oxygen-free vacuum as described above, which also served to reduce the temperature and avoid oxidative degradation of the solvent or solvent/cosolvent mixture. The higher the vacuum (i.e., lower absolute pressure) the lower the temperature and the less amide formation and oxidative degradation. Desirably a vacuum of less than 10 psia, desirably between about 0.1 psia and 5 psia, and more preferably, a vacuum of 4 psia or less is useful in this distillation step to further reduce the boiling point of the solvent/acid/water mixture, further reducing amide formation and enhancing recovery of the acetic acid. As yet a further advantage of the use of the modified solvent/ azeotroping cosolvent mixture of this invention is the use of two distillation columns to accomplish enhanced efficiency of acetic acid recovery from aqueous phases in comparison to processes of the prior art.

The control of distillation temperature in the processes of this invention to limit solvent degradation may be accomplished by a combination of factors, such as selection of the cosolvent, ratio of solvent to cosolvent and conditions of vacuum for the distillation step. Given the teachings of this specification, one of skill in the art may select the appropriate combination of factors to control the distillation temperature as required. For example, one of skill in the art may readily adjust the temperature and vacuum conditions of the distillation step within the above ranges to achieve a desired efficiency of acetic acid recovery according to this invention. Such modifications are encompassed within the appended claims.

In an alternative "direct contact extraction" method of this invention, rather than separate the cellular materials from the acetic acid and water by filtration or centrifugation prior to extraction, the entire fermentation broth containing cells is introduced directly into an extractor. Among conventional extraction devices are columns with either the solvent phase or aqueous phase as the continuous phase. These columns also have entrances and exits for solvent and aqueous phase culture. The fermentation broth including the bacterial cells flows downward through the solvent filled column and solvent flows upward, countercurrent to the broth. The opposite flow can also occur with the water-filled column. These columns differ depending upon the type of packing in the column and sizes of same. Alternatively, other extraction devices, like mixing and settling tanks can be used to accomplish the same tasks, and are readily selected by one of skill in the art without undue experimentation to accomplish this step as taught herein.

The presence of the solvent continuously separates the acetic acid and a small amount of water into a "solvent phase", from the heavier phase containing bacteria and nutrient media, acetate salts, a small amount of acetic acid, and other heavier materials in the aqueous phase. The solvent phase containing acetic acid and a small amount of water is continuously removed and passed to a first distillation column, and then further distilled as described in the embodiment immediately above. The aqueous phase containing the cellular materials exits the bottom of the extractor. Because the aqueous phase and the solvent phase are substantially immiscible, they separate naturally along the column, aided also by the operation of gravity. No other solid-liquid separation methods are used. The heavier aqueous phase is recycled to the bioreactor/fermenter. Any cellular or proteinaceous material formed at the culture/solvent interface is periodically removed from the extractor. Various speeds and directions of solvent or water flows may be adjusted depending on the type of extractor selected.

An example of the extractive fermentation method first described above is represented in Example 6. Examples of the direct contact extraction method are shown in Example 4, which employs a solvent-filled column and Example 5, which uses an aqueous filled column. The aqueous filled system is a less expensive alternative to a solvent filled column, requiring less solvent than the solvent-filled system. Both columns are commercial alternatives.

One of skill in the art is expected to readily alter the specific conditions under which the extractive fermentation and direct extraction methods of this invention function without departing from the scope of this invention.

D. Carbon Dioxide Stripping

According to yet another embodiment of this invention, the process of microbial fermentation of a gas stream (particularly a gas stream containing carbon monoxide, carbon monoxide and hydrogen and optionally carbon dioxide, or carbon dioxide and hydrogen) to produce acetic acid or another product, e.g., an alcohol, salt etc., may be modified to increase its efficiency by substantially reducing from the fermentation broth the presence of any carbon dioxide and optionally sulfur (in the form of hydrogen sulfide). In microbial fermentations of such gases, such as those of the prior art (see PCT WO98/00558) or those taught herein, carbon dioxide and hydrogen sulfide are present both in the gas stream exiting the fermenter/bioreactor and in the liquid fermentation broth exiting from the fermenter/bioreactor to the next step in the process. For example, at 6 atmospheres pressure in the fermenter (~75 psig) the exit gas contains about 50 percent $CO_2$ and 700 ppm $H_2S$, and the fermentation broth contains roughly 3 g/L $CO_2$ and 0.01 g/L $H_2S$. During extraction, the $CO_2$ and $H_2S$ are removed along with acetic acid by the solvent. This is true for processes employing conventional amine solvents, as well as for the use of the modified solvent/cosolvent mixtures described in this invention.

Anything that is extracted into the solvent, reduces the solvent capacity for the acid. Because the concentration of $CO_2$ in the fermentation broth is similar to the concentration of acetic acid (5 g/L) in the fermentation broth, it represents a real threat to acetic acid loading in the solvent. Thus, the $CO_2$ present in the fermentation broth limits the loading potential of the solvent for acetic acid. Hydrogen sulfide is not a significant threat to acetic acid loading because of its low concentration, but $H_2S$ as sulfide ion is an essential nutrient for the culture. The removal of sulfur from the fermenter in the fermentation broth also reduces the available sulfur for the bacteria in the fermenter. Although it appears that the exhaust gas from the reactor has hydrogen sulfide and therefore is in itself removing sulfur, having the sulfur extracted increases the cost for sulfur as a nutrient. Similarly since carbon dioxide is required for conversion of hydrogen to acetic acid, its removal in the fermentation broth during the production process reduces the utilization of hydrogen.

Therefore, the present invention provides an improved method of microbial fermentation of gases for the production of acetic acid by including as a step of the process the removal of carbon dioxide from the fermentation broth prior to extraction. An optional, but desirable step involves the removal of hydrogen sulfide from the fermentation broth prior to extraction. Preferably, both carbon dioxide and hydrogen sulfide are removed from the fermentation broth, and optionally returned to the fermenter.

One embodiment of this process involves contacting the fermentation broth (which may be composed of bacterial cells, acetic acid, nutrient media, salts and other components from the fermentation) or the cell-free stream (which may have been first filtered or centrifuged to remove most of the bacterial cells and other heavier materials therefrom) with a "stripping" gas stream that is devoid of carbon dioxide and preferably devoid of hydrogen sulfide. This "stripping" gas can include, without limitation, nitrogen, helium, argon, methane or the original dilute gas it is contains little to no carbon dioxide and preferably no hydrogen sulfide. Essentially any non-reactive gas or mixture of non-reactive gases is useful in this context. Introduction of the stripping gas, e.g., $N_2$, to the fermentation broth or cell-free stream exiting the fermenter reverses the equilibrium between the dissolved $CO_2$ (or $H_2S$) in the liquid phase and the gas phase, and strips the gases from the liquid phase. The preferred method of contact with the stripping gas is in a countercurrent stripper column. Just as equilibrium exists between the $CO_2$ (or $H_2S$) gas that is dissolved in the fermentation liquid exiting the fermenter, an equilibrium is also established between the broth or cell-free stream entering the countercurrent column and the gas leaving therefrom. As the stripping gas and the $CO_2$ laden fermentation broth or cell-free stream contact each other, equilibrium between the stripping gas, e.g., $N_2$, and the $CO_2$ in the water is continually updated. The packing in the column ensures good surface area between the liquid and the stripping gas.

Figure 3:
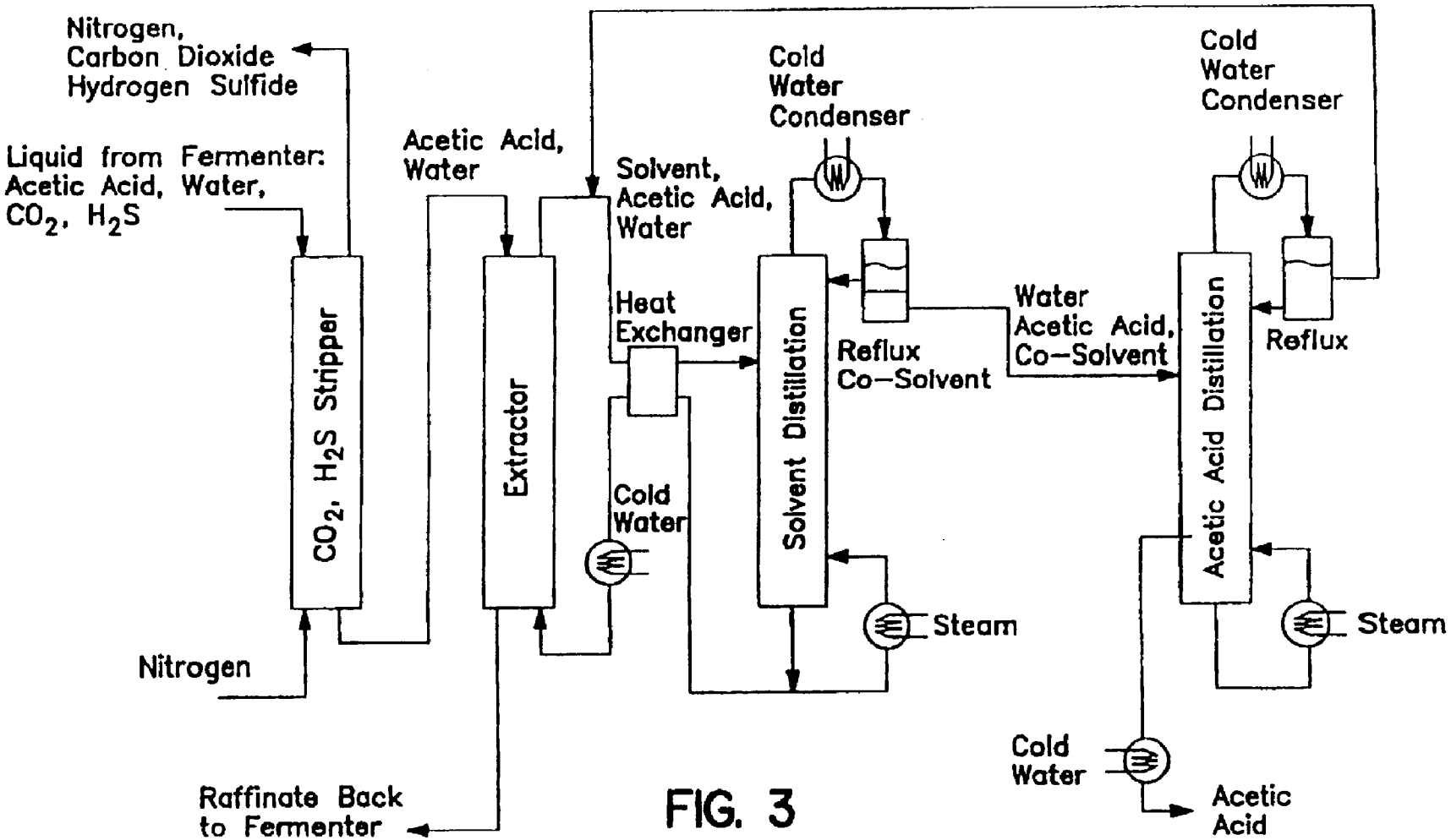
FIG. 3 is a schematic drawing of an exemplary apparatus set-up useful for the microbial fermentation of gases for the production of acetic acid, using the modified process step of carbon dioxide and hydrogen sulfide stripping of the fermentation broth prior to extraction and also employing only two distillation columns. See, e.g., Example 6. The auxiliary apparatus which controls the temperature of the various stages of this production process are identified in the figure as cold water condensers, heat exchangers or steam.

Although the liquid exiting the countercurrent column at the bottom has had its $CO_2$ concentration significantly reduced, the fresh nitrogen stripping has coming in has complete capacity for reaching equilibrium with the $CO_2$ in the water. When the nitrogen finally leaves the top of the stripper column, it is saturated with $CO_2$ (and $H_2S$). The $CO_2$ (or $H_2S$) laden nitrogen can be scrubbed to remove or recycle the $CO_2$ and $H_2S$ back to the fermenter. The "stripped" or scrubbed fermentation broth or cell-free stream then enters the next step of the acetic acid production process, e.g., the extraction with solvent or the contact with solvent in the direct extraction process described above, and distillation. See, e.g., the schematic drawing of FIG. 3 and Example 6A.

Still another embodiment of this aspect of the invention is provided by altering the method of the carbon dioxide stripping. As exemplified in Example 6C, this process involves subjecting the fermentation broth (which may be composed of bacterial cells, acetic acid, nutrient media, salts and other components from the fermentation) or the cell-free stream (which may have been first filtered or centrifuged to remove most of the bacterial cells and other heavier materials therefrom) to a rapid decrease in pressure prior to introduction into the extractor or into a solvent extraction column. For example, the pressure of the fermentation broth or cell-free stream may be decreased from 6 atmospheres (or greater) to a lower pressure, e.g., atmospheric pressure, which causes the carbon dioxide in the broth or cell-free stream to approach its equilibrium concentration. Preferably this decrease in pressure occurs after the fermentation broth or cell-free stream exits the fermenter and is in a separate container. The $CO_2$ is preferably recycled back to the fermenter.

The "stripped" fermentation broth or cell-free stream then enters the next step of the acetic acid production process, e.g., the extraction with solvent or the contact with solvent in the direct extraction process described above, and distillation. See, e.g., Example 6C.

Yet a further embodiment of this aspect of the invention is provided by altering the method of the carbon dioxide stripping. As exemplified in Example 6D, this process involves removing the fermentation broth (which may be composed of bacterial cells, acetic acid, nutrient media, salts and other components from the fermentation) or the cell-free stream (which may have been first filtered or centrifuged to remove most of the bacterial cells and other heavier materials therefrom) from the fermenter, and heating the broth or cell-free stream to a temperature of about 80° C. or more prior to extraction. The high temperature causes the carbon dioxide in the broth or cell-free stream to approach its equilibrium concentration. The $CO_2$ and $H_2S$ preferably are recycled to the fermenter via a variety of common engineering methods.

The "stripped" fermentation broth or cell-free stream then enters the next step of the acetic acid production process, e.g., the extraction with solvent or the contact with solvent in the direct extraction process described above, and distillation. See, e.g., Example 6D The only disadvantage of this modification of the process is that after extraction, the aqueous broth component cannot be recycled back into the fermenter, due to the killing effect of the heating temperature upon the bacteria, and must be discarded.

One of skill in the art is expected to readily alter the specific conditions under which the carbon dioxide and optionally hydrogen sulfide stripping occurs departing from the scope of this invention.

The following examples illustrate various aspects of this invention and do not limit the invention, the scope of which is embodied in the appended claims.

EXAMPLE 1

Recovery of Acetic Acid from the Fermentation Product Stream Using the Solvent/Azeotroping Cosolvent Mixture of the Invention A. 60% Modified Solvent A and 40% Orfom® SX-18 Cosolvent An apparatus and method for producing acetic acid from a variety of aqueous gaseous streams is described in detail in published International Patent Application No. PCT WO98/00588, incorporated by reference herein. The process described therein is modified according to one aspect of the present invention, as follows.

A gas stream containing 45% carbon monoxide, 45% hydrogen and 10% carbon dioxide was introduced into a continuous stirred tank fermenter containing C. ljungdahlii strain ER12 and suitable nutrient medium. The liquid product stream from the fermenter with cell recycle (i.e., cell separation utilizing a hollow fiber membrane) containing 5 g/l free acetic acid and 5 g/l acetate at pH 4.75 (i.e., the cell-free stream) was sent to a multi-state countercurrent extraction column. In the extraction column, the cell-free stream is contacted with a solvent/cosolvent mixture of this invention containing 60% Modified Solvent A and 40% Orfom® SX-18 cosolvent at a temperature of 37° C. and using a 0.09 (v/v) solvent to feed ratio. The solvent exiting the extractor contained 50 g/l acetic acid, and the aqueous stream (which was sent back to the fermenter as recycle) contained 5 g/l acetate and 0.5 g/l acetic acid.

The solvent stream containing the modified solvent/cosolvent and acetic acid was sent to a distillation system containing a first "solvent" column, an accumulator and a second "acid" column. In operating the first distillation column, the combination of a low-boiling co-solvent and a mild vacuum of 0.3 atm pressure permits the column temperature to be minimized and permits the separation of acid, water and cosolvent in the overhead product from the Modified Solvent A and some co-solvent, which stay in the bottom of the column. The bottom temperature is kept at a maximum temperature of 130° C. by vacuum operation. The modified solvent and cosolvent at the bottom of the column are sent back to the extractor as recycle. The mixture at the top of the column, i.e., water, acetic acid and some co-solvent, separates at the top of the column and is then cooled to allow the co-solvent to condense and separate from the water/acid.

By removing most of the co-solvent from the water/acid, the lower co-solvent concentration in the water/acid is below the azeotrope. This mixture, which contains acetic acid and water and a small amount of cosolvent, is sent to the second "acid" distillation column. In this second column, the water and co-solvent and some acid go out the top of the column and the acetic acid goes to the bottom which has a temperature of 118° C. Part of the water/acid phase is refluxed to the column and the remaining water/acid phase and co-solvent are recirculated back to extraction. Glacial acetic acid is removed near the bottom of this column as product, and the overhead is sent back to the process as recycle.

B. 30% Adogen283®LA (Witco) Solvent and 70% SX-18 Cosolvent

As another example of a fermentation method conducted according to the present invention, the liquid product stream described in Part A containing 5 g/l free acid and 10 g/l acetate at pH 5.0 was contacted with a solvent mixture containing 30% Adogen283®LA solvent (Witco) and 70% SX-18 cosolvent in a multi-state extractor. A 0.09 solvent to feed ratio is used. The solvent exiting the extractor contains 25 g/l acetic acid and the aqueous stream contains 10 g/l acetate and 2.75 g/l acetic acid. Thus, the acid distribution coefficient is reduced by dilution with additional SX-18 cosolvent. The process for product recovery by distillation is thereafter the same as described above.

C. 30% Modified Solvent A and 70% Decane Cosolvent

An extraction similar to that of Part B was carried out with 30% Modified Solvent A in a cosolvent, decane. The distribution coefficient remains the same as in Part B, and the process for product recovery by distillation is equivalent.

D. 60% Adogen283®LA (Witco) solvent and 40% n-dodecane Cosolvent

The extraction of Part A is carried out with 60% Adogen283®LA solvent (Witco) in n-dodecane cosolvent. The extraction process remains the same as in Part B, yielding 50 g/l acid in the solvent, and 10 g/l acetate and 0.5 g/l acetate acid in the aqueous phase.

The aqueous stream containing acetate is again sent back to the fermenter as recycle. The solvent stream containing acetic acid is sent to a distillation system very similar to the system presented in Part B, except that the pressure in the solvent column is 0.2 atmosphere and the temperature at the bottom of the column is 127° C.

EXAMPLE 2

Amide Formation

This example demonstrates the basis for the invention, that is, determination by the inventors that temperature control is vital to the efficient functioning of an amine-containing solvent in an acetic acid production process when an amine-containing solvent is employed in distillation and extraction steps.

The amide formation from amine in the solvent is a first order rate expression in acetic acid concentration illustrated by the formula: Y=kX, where Y represents amide concentration after 16 hours, measured in weight percent; X=acetic acid concentration after 16 hours, measured in weight percent, and k=the amide formation rate constant.

The rate of amide formation and thus the rate constant, k, increases with temperature by an Arrhenius type rate expression, represented by the formula:

$$\ln(k)=-9163.21\ (1/T)+27.41,$$

where T=the absolute temperature in Kelvin.

Figure 4:
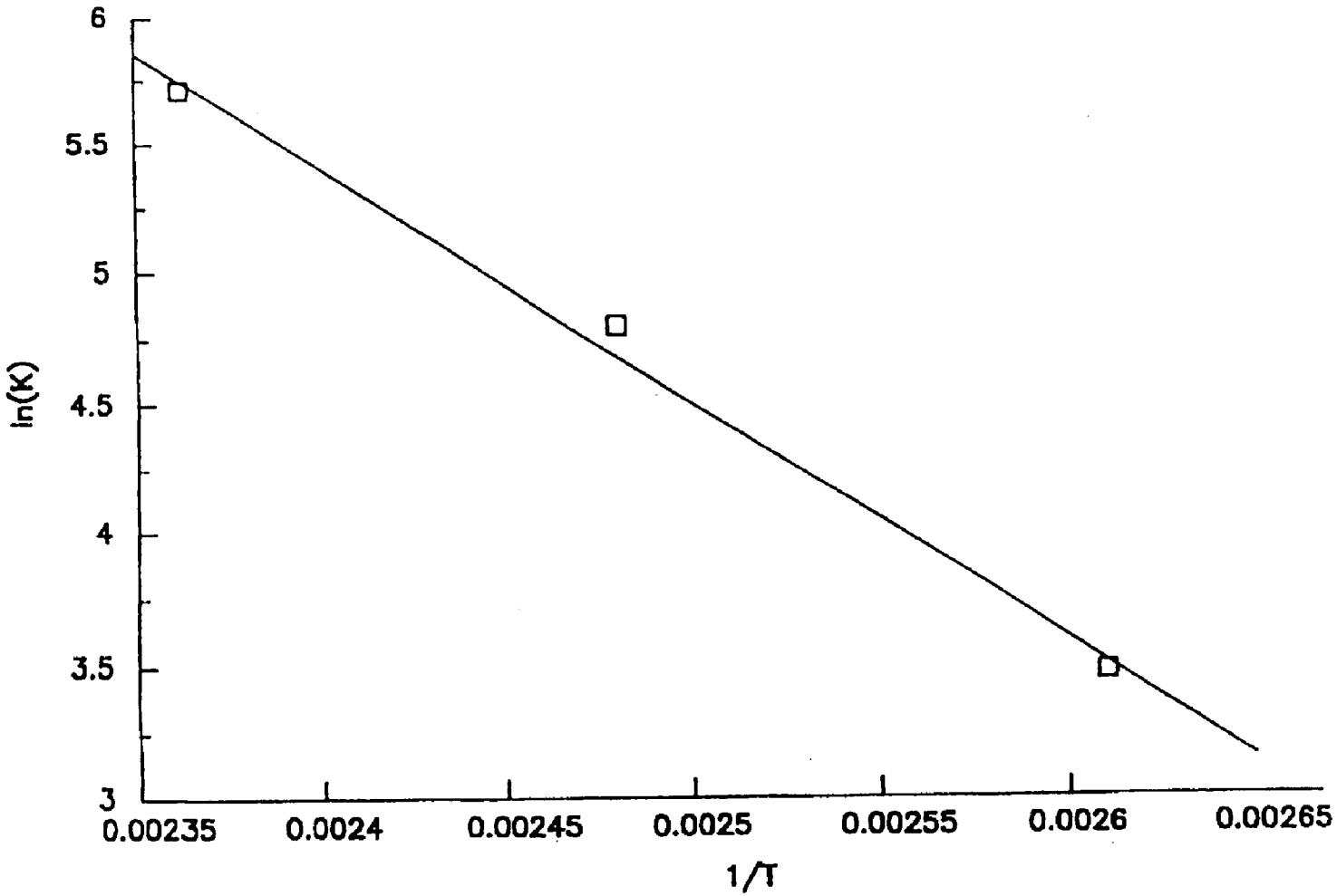
FIG. 4 is a graph illustrating amide formation rate temperature dependency, according to the formula Y=kX, wherein Y is the amide concentration after 16 hours in weight per cent; X is the acetic acid in the feed in weight per cent; and k is the amide formate rate constant. The formula for which points are noted on the graph is ln(k)=−9163.21 (1/T)+27.41, where T is the absolute temperature in Kelvin. See, e.g., Example 2 below.

FIG. 4 illustrates a plot of ln(k) as a function of the inverse absolute temperature which is used in finding the Arrhenius rate expression. For example, at a temperature of 150° C. (1/T=0.00236), the rate of amide formation is 9 times greater than at a temperature of 110° C. (1/T=0.00261)

EXAMPLE 3

Direct Extraction of Acetic Acid Using a Continuous Solvent Phase Column

Fermentation broth obtained from a fermenter similar to that of Example 1 contained 2.6 g/l cells (dry weight), excess nutrients, 5 g/l acetic acid and 5.0 g/l acetate at pH 4.75. This broth is sent to a continuous solvent phase extraction column containing 60% Adogen283®LA (Witco) solvent in SX-18 cosolvent. The extraction column is a cylindrical column, packed or unpacked, which has entrances and exits for solvent and aqueous phase culture. Culture flows downward through the solvent filled column, and solvent flows upward, countercurrent to the culture. The exiting solvent from the column contains 50 g/l acetic acid and is sent to distillation for acid recovery prior to recycle back to the column. The exiting culture stream at the bottom of the column contains 5.0 g/l acetate, 0.5 g/l acetic acid, cells and nutrients and is sent back to the fermenter as recycle. Because the solvent and culture are immiscible, little to no water (culture) is present in the solvent and little to no solvent is present in the culture recycle stream. A small rag layer consisting of cellular proteinaceous material is formed at the culture/solvent interface which must be removed periodically.

EXAMPLE 4

Extraction of Acetic Acid Using a Continuous Aqueous Phase Column

The fermentation broth of Example 3 is passed through a continuous aqueous phase extraction column containing 60% Adogen283®LA solvent (Witco) in SX-18 cosolvent. The column is constructed similarly as in Example 3 except that the column is filled with aqueous phase culture instead of solvent. Again solvent and culture flow countercurrently, with solvent exiting the top of the column and culture exiting the bottom of the column. Exiting aqueous phase and solvent phase concentrations are the same as in Example 3.

EXAMPLE 5

Internal Extractive Fermentation for Acetic Acid Production from CO, $CO_2$ and $H_2$ Industrial waste gas containing 7.52 percent carbon dioxide, 31.5 percent carbon monoxide, 27.96 percent hydrogen and 33.02 percent nitrogen is fermented to acetic acid/acetate at pH 5.0 in a fermenter/reactor as described in Example 1A, using Clostridium ljungdahlii, BRI isolate ER12. The gas retention time (ratio of reactor volume to gas flow rate) is 10 minutes and the liquid dilution rate (ratio of liquid medium flow rate to reactor volume) is 0.03 $hour^{-1}$. Medium containing essential vitamins and minerals flows continuously into the reactor. The agitation rate is 1000 rpm. The reactor also contains a solvent phase of 60% Modified Solvent A of this invention in SX-18 cosolvent. As the culture produces acetic acid from CO, $CO_2$ and $H_2$, it is extracted by the solvent.

A mixture of solvent and culture exit the fermenter and are separated in a small settling tank. A portion of the aqueous phase, equal in rate to the medium feed rate, flows from the system as waste purge. The balance of the aqueous phase from the separator is returned to the reactor. Solvent containing extracted acid is sent to distillation for recovery. After recovery the solvent is recycled to the reactor.

EXAMPLE 6

Stripping of Culture Prior to Acid Extraction

A. Nitrogen Stripping

Culture from the reactor of Examples 1–4 containing bacterial cells, 5 g/l acetic acid, 9.3 g/l acetate and dissolved sulfide and carbonate at pH 5.0 is passed through a nitrogen stripping column to remove dissolved $CO_2$ and sulfide as $H_2S$ before passing the culture through an extraction column. This operation is required in order to prevent solvent loading of $CO_2$ and $H_2S$ instead of acetic acid, and to return $H_2S$ as a sulfur source and reducing agent back to the culture. The $N_2$ gas stream which contains $H_2S$ and $CO_2$ is sent back to the reactor as a secondary gas feed. By using the nitrogen stripper, the solvent is loaded to 50 g/l acetic acid. Without $CO_2$ and $H_2S$ removal prior to extraction, the solvent is loaded to 25–30 g/l acetic acid.

B. Stripping with Alternative Gases

The culture of Part A is stripped with gases other than $N_2$, including methane or $CO_2$-free synthesis gas containing $H_2$, CO, $CH_4$. All other aspects of the example are the same.

C. Stripping via Pressure Reduction to Relieve Dissolved $CO_2$

The pressure of the fermentation broth in Part A is rapidly decreased from 6 or 3 atmospheres to atmospheric pressure in order to release $CO_2$ prior to loading in the extractor. The $CO_2$ pressure in the culture approaches the equilibrium concentration according to Henry's law at one atmosphere, a greatly reduced level which helps maximize acid extraction by the solvent.

D. Stripping via Preheating to Relieve Dissolved $CO_2$

The cell-free stream in Part A is preheated prior to extraction to relieve $CO_2$ in much the same manner as noted in Part C. The broth cannot be reused after heating.

All published documents are incorporated by reference herein. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A water-immiscible solvent/co-solvent mixture comprising:

(a) a water-immiscible solvent comprising greater than 50% by volume of a mixture of isomers of highly branched di-alkyl amines, and [from] *less than* about [0.01% to 20%] *1%* by volume of mono-alkyl amines said solvent having a coefficient of distribution greater than 10; and (b) at least 10% by volume of a non-alcohol co-solvent having a boiling point lower than the boiling point of said solvent (a), wherein said mixture extracts acetic acid from aqueous streams.

2. The mixture according to claim 1 wherein said co-solvent is immiscible with water and readily separates therefrom, and has low toxicity to anaerobic acetogenic bacteria.

3. The mixture according to claim 1 wherein said co-solvent forms an azeotrope with water and acetic acid.

4. The mixture according to claim 1 wherein said co-solvent comprises a hydrocarbon having from 9 to 11 carbon atoms.

5. The mixture according to claim 1 wherein said solvent (a) contains greater than 80% by volume said di-alkyl amines and is reduced to less than about 1% by volume of low boiling compounds and mono-alkyl amines wherein said low boiling compounds boil at or below 115° C. at 69.9 Torr.

6.The mixture according to claim 1 wherein said solvent (a) contains from about 1% to 10% by volume tri-alkyl amines.

7. The mixture according to claim 1, wherein said solvent (a) is produced by distilling from a solvent containing low boiling compounds, mono-alkyl amines, di-alkyl amines and tri-alkyl amines substantially all low boiling compounds and monoalkyl amines to improve acetic acid extractive capacity wherein said low boiling compounds boil at or below 115° C. at 69.9 Torr.

8. The mixture according to claim 7, wherein said solvent (a) is produced by subjecting said distilled solvent to a second distillation to reduce substantially all tri-alkyl amines.

9. A process for obtaining acetic acid from an aqueous phase comprising acetic acid comprising the steps of:

(a) contacting the aqueous phase with the solvent/co-solvent mixture [of claim 1] *comprising:*

(*i*) *a water-immiscible solvent comprising greater than 50% by volume of a mixture of isomers of highly branched di-alkyl amines, and from about 0.01% to 20% by volume of mono-alkyl amines said solvent having a coefficient of distribution greater than 10; and*

(*ii*) *at least 10% by volume of a non-alcohol co-solvent having a boiling point lower than the boiling point of said solvent* (*i*)*, wherein said mixture extracts acetic acid from aqueous streams;*

(b) extracting acetic acid from said aqueous phase into the resulting solvent phase; and (c) distilling acetic acid from said solvent phase under a temperature not exceeding 160° C.

10. An anaerobic microbial fermentation process for the production of acetic acid, said process comprising the steps of:

(a) fermenting in a bioreactor an aqueous stream comprising an anaerobic acetogenic bacteria in a nutrient medium and a gas stream comprising at least one gas selected from the group consisting of (1) carbon monoxide, (2) carbon dioxide and hydrogen, (3) carbon monoxide, carbon dioxide and hydrogen; and (4) carbon monoxide and hydrogen; thereby producing a fermentation broth comprising acetic acid;

(b) separating said bacteria from other components in said broth to provide a substantially cell-free stream;

(c) continuously extracting acetic acid from said cell-free stream into a solvent phase by contacting said cell-free stream with a solvent mixture of claim 1; and (d) continuously distilling from the product of (c) the acetic acid separately from the solvent phase under a temperature not exceeding 160° C.;

wherein said extracting and distilling steps occur without substantially degrading said amine to an amide, thus enhancing the efficiency of production of acetic acid.

11. The process according to claim 10 wherein said separating step employs a centrifuge, a hollow fiber membrane, or a solid-liquid separation device.

12. The process according to claim 10 further comprising as step (e) recycling said solvent to the distillation device of step (d) and said cell-free stream to said bioreactor in step (a).

13. The process according to claim 10 wherein said distillation step occurs in a substantially oxygen-free vacuum.

14. The process according to claim 10 wherein step (d) further employs a vacuum between about 0.5 to about 10 psia.

15. The process according to claim 10 wherein said anaerobic bacteria is selected from the group consisting of Acetobacterium kivui, A. woodii, Butyribacterium methylotrophicum, Clostridium aceticum, C. acetobutylicum, C. formoaceticum, C. kluyveri, C. thermoaceticum, C. thermocellum, C. thermosaccharolyticum, Eubacterium limosum, Peptostreptococcus productus, and C. ljungdahlii, and mixtures thereof.

16. The process according to claim 15 wherein said C. ljungdahlii is selected from the strains consisting of: PETC ATCC 55383, O-52 ATCC 55989, ERI2 ATCC 55380 and C-01 ATCC 55988, and mixtures thereof.

17. A method for enhancing the efficiency of acetic acid recovery from a fermentation broth comprising an aqueous stream containing an anaerobic acetogenic bacterium and nutrient medium, said bacterium having been fermented in the presence of a gas stream comprising at least one gas selected from the group consisting of (1) carbon monoxide, (2) carbon dioxide and hydrogen, (3) carbon monoxide, carbon dioxide and hydrogen; and (4) carbon monoxide and hydrogen; said method comprising contacting said stream with a solvent mixture of claim 1; continuously extracting said acetic acid from said stream in said solvent mixture; and distilling said acetic acid from said solvent at a distillation temperature not exceeding 160° C. therefrom, without substantially degrading said amine to amide.

18. An anaerobic microbial fermentation process for the production of acetic acid, said process comprising the steps of:

(a) providing in a fermenter an anaerobic acetogenic bacterium in a nutrient mixture and a solvent mixture of claim 1 for a time sufficient to acclimate said bacteria to said solvent;

(b) introducing into said fermenter an aqueous stream comprising at least one gas selected from the group consisting of (1) carbon monoxide, (2) carbon dioxide and hydrogen, (3) carbon monoxide, carbon dioxide and hydrogen, and (4) carbon monoxide and hydrogen; and producing a fermentation broth comprising said bacteria, nutrient medium, acetic acid, solvent and water;

(c) introducing said fermentation broth into a settling tank, wherein an aqueous phase containing said bacteria and nutrient medium settles to the bottom of said tank from the solvent phase which contains acetic acid, solvent and water, without filtration;

(d) continuously distilling from the solvent phase of (c) the acetic acid separately from the solvent phase under a temperature not exceeding 160° C.;

wherein said distilling step occurs without substantially degrading said amine to an amide, thus enhancing the efficiency of acetic acid production.

19. The process according to claim 18 further comprising recycling said solvent and said aqueous phase containing said bacteria into said fermenter.

20. The process according to claim 19 wherein said distillation step occurs in a substantially oxygen-free vacuum.

21. The process according to claim 18 wherein step (d) further employs a vacuum between about 0.5 to about 10 psia.

22. The process according to claim 18 wherein said anaerobic bacteria is selected from the group consisting of Acetobacterium kivui, A. woodii, Butyribacterium methylotrophicum, Clostridium aceticum, C. acetobutylicum, C. formoaceticum, C. kluyveri, C. thermoaceticum, C. thermocellum, C. thermosaccharolyticum, Eubacterium limosum, Peptostreptococcus productus, and C. ljungdahlii, and mixtures thereof.

23. The process according to claim 22 wherein said C. ljungdahlii is selected from the strains consisting of PETC ATCC 55383, O-52 ATCC 55989, ERI2 ATCC 55380 and C-01 ATCC 55988, and mixtures thereof.

24. An anaerobic microbial fermentation process for the production of acetic acid, said process comprising the steps of:

(a) fermenting in a bioreactor an aqueous stream comprising a nutrient mixture with an anaerobic acetogenic bacteria and at least one gas selected from the group consisting of (1) carbon monoxide, (2) carbon dioxide and hydrogen, (3) carbon monoxide, carbon dioxide and hydrogen; and (4) carbon monoxide and hydrogen; thereby producing a broth comprising acetic acid, water, and bacterial cells;

(b) introducing into an extraction device containing either a continuous solvent phase or a continuous aqueous phase and having exits and entrances therefrom, (i) said broth with no cell separation and (ii) a solvent comprising a solvent mixture of claim 1; wherein a solvent phase containing acetic acid, solvent and water exits said extraction device separately from an aqueous phase comprising said bacteria and nutrient media;

(c) continuously distilling from the solvent phase of (b) the acetic acid and water separately from the solvent at a temperature not exceeding 160° C.;

wherein said steps (b) and (c) occur without substantially degrading said amine to an amide, thus enhancing the efficiency of acetic acid production.

25. The process according to claim 24 wherein said step (b) comprises introducing said solvent into said extraction device in a flow concurrent or countercurrent of that of said broth.

26. The process according to claim 24 further comprises recycling said solvent and said aqueous phase containing said bacteria into said fermenter.

27. The process according to claim 24 wherein said distillation step occurs in a substantially oxygen-free vacuum.

28. The process according to claim 24 wherein step (c) further employs a vacuum between about 0.5 to about 10 psia.

29. The process according to claim 24 wherein said anaerobic bacteria is selected from the group consisting of Acetobacterium kivui, A. woodii, Butyribacterium methylotrophicum, Clostridium aceticum, C. acetobutylicum, C. formoaceticum, C. kluyveri, C. thermoaceticum, C. thermocellum, C. thermosaccharolyticum, Eubacterium limosum, Peptostreptococcus productus, and C. ljungdahlii, and mixtures thereof.

30. The process according to claim 29 wherein said C. ljungdahlii is selected from the strains consisting of PETC ATCC 55383, O-52 ATCC 55989, ERI2 ATCC 55380 and C-01 ATCC 55988, and mixtures thereof.

31. An anaerobic microbial fermentation process for the production of acetic acid, said process comprising the steps of:

(a) fermenting in a bioreactor an aqueous stream comprising at least one gas selected from the group consisting of (1) carbon monoxide, (2) carbon dioxide and hydrogen, (3) carbon monoxide, carbon dioxide and hydrogen; and (4) carbon monoxide and hydrogen; in a nutrient mixture with an anaerobic acetogenic bacteria, thereby producing a fermentation broth comprising acetic acid and dissolved carbon dioxide;

(b) removing said carbon dioxide from the fermentation broth prior to extraction;

(c) contacting said broth (b) with a solvent mixture comprising:

(i) a water-immiscible solvent comprising greater than 50% by volume of a mixture of isomers of highly branched di-alkyl amines, and [from] *less than* about [0.01% to 20%] *1*% by volume of mono-alkyl amines said solvent having a coefficient of distribution greater than 10; and (ii) at least 10% by volume of a non-alcohol co-solvent having a boiling point lower than the boiling point of said solvent (i);

wherein a solvent phase is formed and comprises acetic acid, said solvent and water; and (d) continuously distilling acetic acid from said solvent phase.

32. The process according to claim 31 wherein said distilling step occurs at a temperature not exceeding 160° C., without substantially degrading said amine to an amide, thus enhancing the efficiency of production of acetic acid.

33. The process according to claim 31 wherein said distillation step occurs in a substantially oxygen-free vacuum.

34. The process according to claim 32 wherein said distilling step further employs a vacuum between about 0.5 to about 10 psia.

* * * * *

UNITED STATES PATENT AND TRADEMARK OFFICE

Certificate

Patented: July 11, 2006

Patent No. RE39,175 E

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James L. Gaddy, Fayetteville, AR (US); and Ching-Whan Ko, Fayetteville, AR (US).

Signed and Sealed this Eighth Day of July 2008.

JON P. WEBER
*Supervisory Patent Examiner*
Art Unit 1657